United States Patent [19]

Burgin

[11] 4,263,899
[45] Apr. 28, 1981

[54] LOCKING ADJUSTABLE SPECULUM

[76] Inventor: Kermit H. Burgin, Box 334, Whitestone, Ind. 46075

[21] Appl. No.: 958,794

[22] Filed: Nov. 8, 1978

Related U.S. Application Data

[63] Continuation-in-part of Ser. No. 901,521, May 1, 1978, Pat. No. 4,156,424.

[51] Int. Cl.³ .......................... A61B 1/06; A61B 17/02
[52] U.S. Cl. ........................................ 128/18; 128/20; 128/341
[58] Field of Search ............................. 128/3, 17–20, 128/341, 345, 242, 244, 303.11, 303.12, 76 D, 15, 16

[56] References Cited

U.S. PATENT DOCUMENTS

| 281,880 | 7/1883 | Hubbell | 128/17 |
|---|---|---|---|
| 605,652 | 6/1898 | Pitt | 128/18 |
| 1,230,873 | 6/1917 | Crossley | 128/20 |
| 1,706,500 | 3/1929 | Smith | 128/20 |
| 2,247,258 | 6/1941 | Shepard | 128/16 |
| 2,977,958 | 4/1961 | Seiger | 128/17 X |
| 3,035,582 | 5/1962 | Seiger | 128/17 X |
| 3,664,330 | 5/1972 | Deutsch | 128/18 |
| 3,749,088 | 7/1973 | Gauthier | 128/20 |
| 3,762,400 | 10/1973 | McDonald | 128/6 X |
| 3,796,214 | 3/1974 | Davis | 128/6 X |
| 3,890,960 | 6/1975 | Wunsch nee Kuhn et al. | 128/16 |
| 3,965,890 | 6/1976 | Gauthier | 128/20 |
| 4,037,588 | 7/1977 | Heckele | 128/16 X |

FOREIGN PATENT DOCUMENTS

| 473451 | 1/1915 | France | 128/20 |
|---|---|---|---|
| 1118877 | 6/1956 | France | 128/15 |
| 62076 | 8/1912 | Switzerland | 128/76 D |

*Primary Examiner*—Robert W. Michell
*Assistant Examiner*—Arthur S. Rose
*Attorney, Agent, or Firm*—Jenkins, Coffey, Hyland, Badger & Conard

[57] ABSTRACT

An adjustable speculum includes a base rotatably supporting a pair of shafts, and a pair of dilating members. Each dilating member has a distal end for contacting and restraining a wall of an orifice or incision and a proximal end for detachably engaging a respective shaft. The base includes a mechanism for adjusting the distance between the shafts whereby the distance between the proximal ends of the dilating members is adjustable. Each shaft includes a portion for preventing the dilating member from rotating with respect to the shaft. The distance between the distal ends of the dilating members is also adjustable.

18 Claims, 15 Drawing Figures

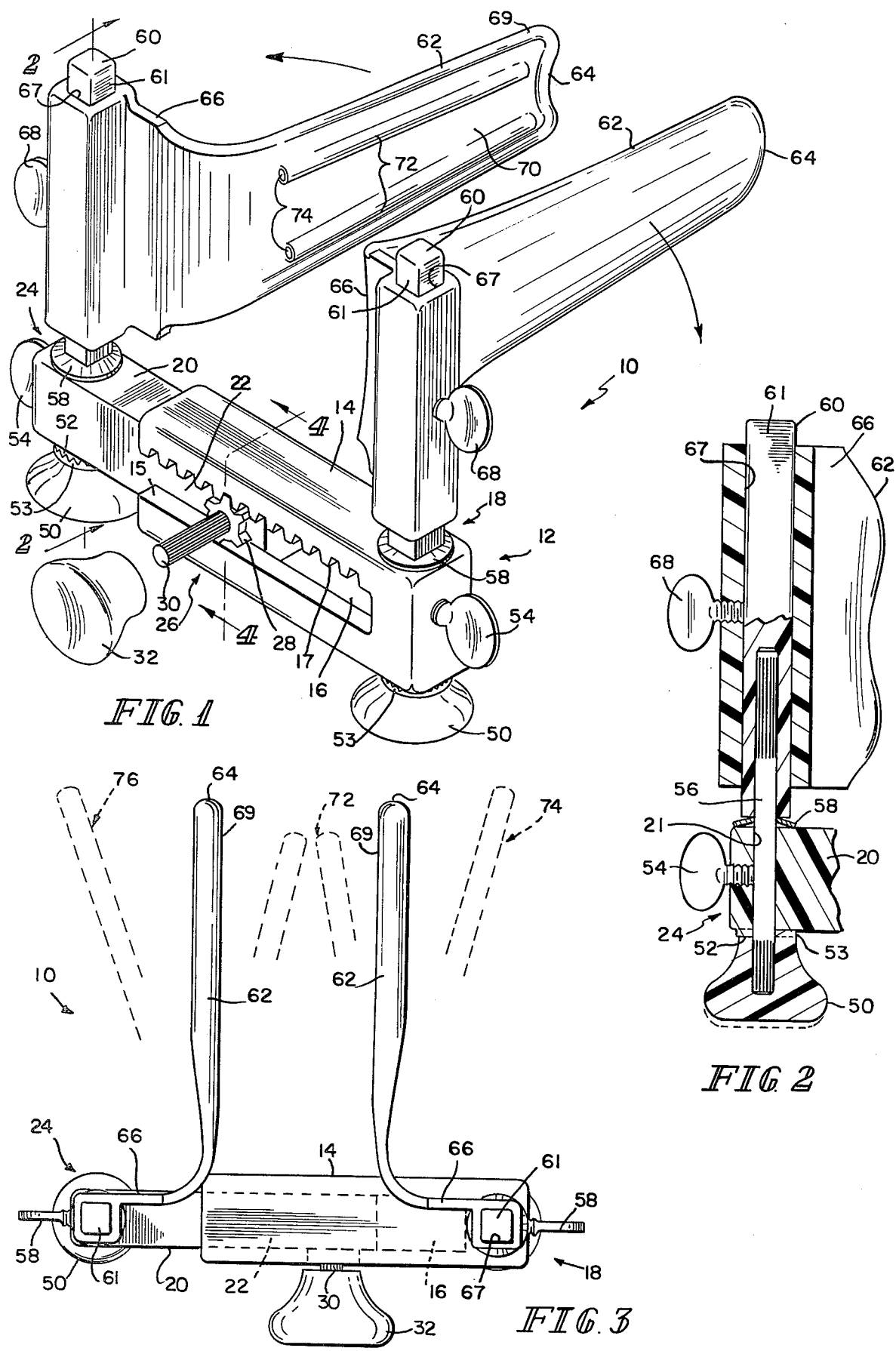

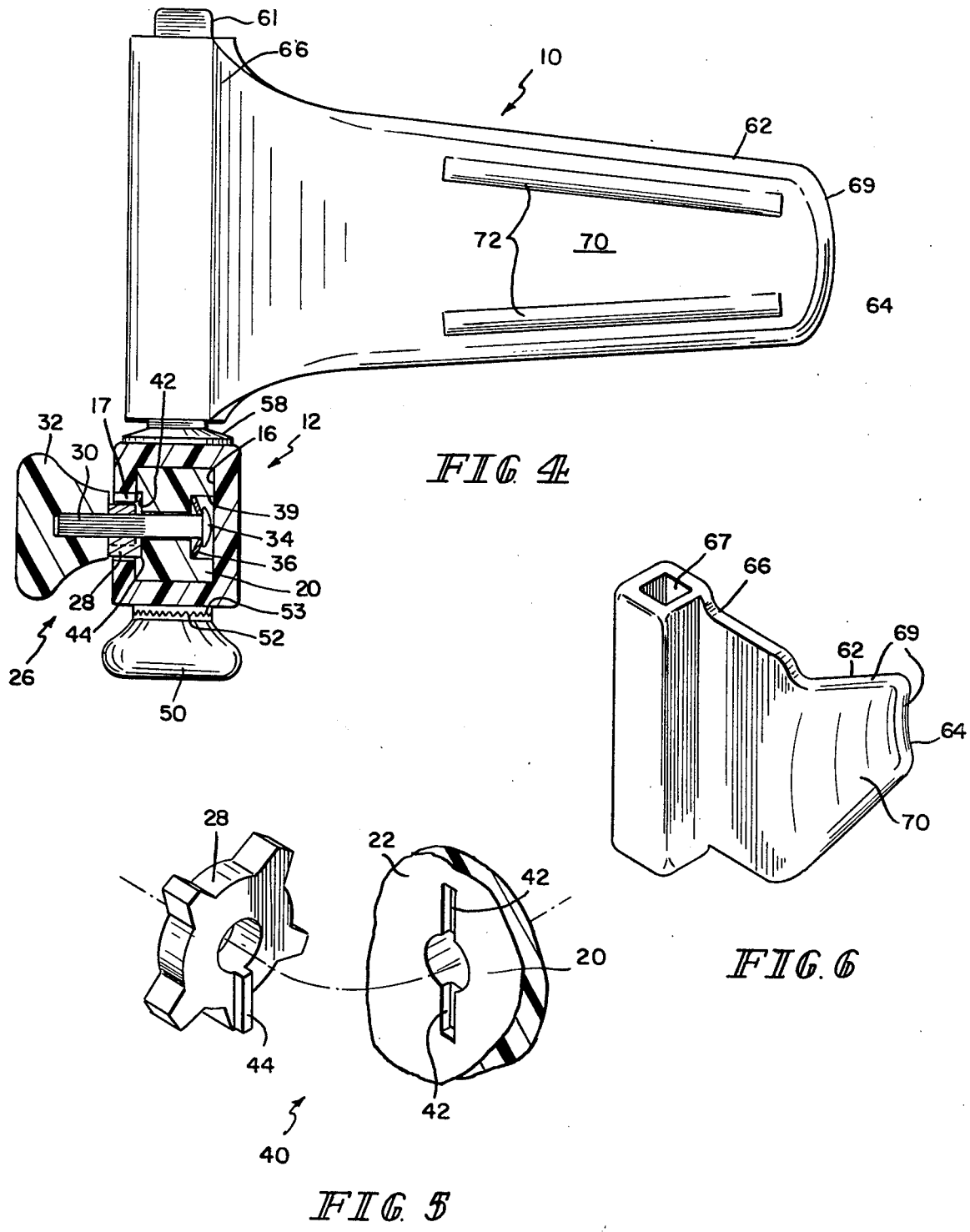

LOCKING ADJUSTABLE SPECULUM

This is a continuation-in-part of my copending United States Patent Application Ser. No. 901,521 filed May 1, 1978, now U.S. Pat. No. 4,156,424.

The present invention relates generally to an apparatus for dilating a meatus, orifice or incision and more particularly to a speculum which provides means for independently adjusting the distances between the proximal and distal ends of detachable restraining members used to dilate the meatus, orifice or incision and means for sustaining various desired distances between both the distal and proximal ends thereby leaving the speculum operator's hands free for purposes of examination or other activities.

There are many known specula and forceps for enlarging body orifices or incisions for such purposes as examination or surgery. However, many of these devices are not adaptable for use in orifices or incisions having different sizes, shapes, depths and so forth; have limited adjustment capability; and have the means for adjustment situated such that the view and/or ability of the user to examine the orifice is at least partially obstructed. The following are illustrative U.S. Pat. Nos.: Molesworth, 400,589; Crockett, 776,302; Joutras, 1,094,575; Radcliff, 2,217,968; Batista, 3,853,120; Marco, 2,544,932; Moore et al, 3,716,047; Moore et al, 3,890,961; Smith, 1,706,500; Rose, 3,196,865; Crossley, 1,230,873; Sheaff, 1,222,478; Pitt, 605,652; and Gentile, French Patent Specification No. 473,451. See also *SURGERY, GYNECOLOGY AND OBSTETRICS*, Vol., 68, No. 6, Jan. 1939, pp. 1060-63; Fogerty et al, U.S. Pat. No. 3,503,398; Galiano, U.S. Pat. No. 399,749; Bernardot, French Patent Specification No. 641,915; and Raffaele, Italian Patent Specification No. 246,611. Furthermore, many prior devices require that the user maintain a constant physical force in order to restrain the orifice once it has been enlarged. See for example Pomerene, U.S. Pat. No. 1,170,324.

In copending applications, Ser. No. 811,550, filed June 30, 1977, now U.S. Pat. No. 4,165,746, and Ser. No. 958,795, filed Nov. 8, 1978, both entitled "Plastic Forceps", I have disclosed solutions to some of the aforementioned problems associated with prior specula or forceps. It is believed that the improved speculum provided by the present invention provides solutions to all of the problems mentioned hereinabove by providing a high degree of flexibility and various self-sustaining features.

In accordance with the present invention, an adjustable speculum is provided. The speculum is adaptable for use in enlarging and holding open orifices, incisions and the like of various sizes, shapes and depths. The speculum allows the user substantially unobstructed access to the orifice for examination and various other functions.

According to the invention, a speculum includes a pair of members for restraining and dilating an orifice, incision or the like. Each restraining member has a distal end for contacting the walls of the orifice and a proximal end for detachably engaging a shaft, and a base supporting the shafts and including means for adjusting the distance between the shafts whereby the distance between the proximal ends of the restraining members is independently adjustable.

Further according to the invention, in such a speculum, the shafts are rotatably coupled to the base and include means fixed to each shaft for preventing the dilating members from rotating on the shafts. The distance between the distal ends of the dilating members is rotatably adjustable independent of adjustments to the proximal ends of the dilating members.

Additionally according to the invention, the speculum includes means for independently sustaining desired distances between the distal and proximal ends of the dilating members and desired positions of the dilating members along the shafts.

Another feature of the present invention is to provide a speculum having detachable dilating members which may be of various sizes or shapes and which may be either separately sterilized or disposed of after each use.

Various features and advantages of the present invention will be apparent from the following detailed description of an embodiment thereof. The description can best be understood by reference to the accompanying drawings which illustrate the invention.

FIG. 1 is a perspective view of an apparatus constructed in accordance with the present invention;

FIG. 2 is a fragmentary cross-sectional view of the apparatus of FIG. 1 taken generally along section lines 2—2 of FIG. 1;

FIG. 3 is a top plan view of the apparatus of FIG. 1;

FIG. 4 is a fragmentary cross-sectional view of the apparatus of FIG. 1 taken generally along section lines 4—4 of FIG. 1;

FIG. 5 is an exploded fragmentary perspective view of a detail of the apparatus shown in the cross-sectional view of FIGS. 1-4;

FIG. 6 is a perspective view of a detail of an alternative structure to that illustrated in FIGS. 1-4;

Figure 7:
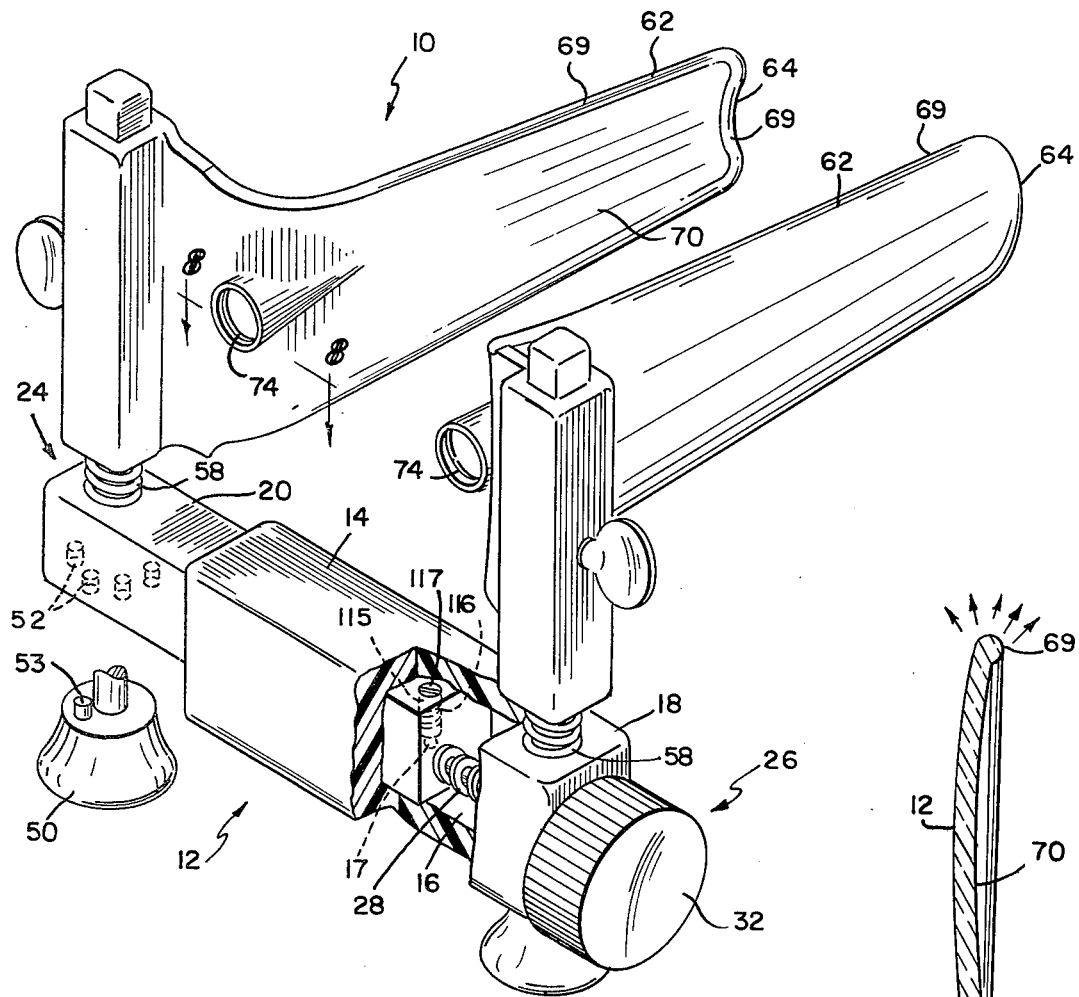
FIG. 7 is a perspective view of another apparatus constructed according to the present invention.

Referring particularly to FIG. 1, a speculum 10 includes a base 12 having first and second members 14 and 20, respectively, adjustably coupled to each other. First member 14 includes a hollow interior 16. A slot 15 is formed in first member 14 as shown, with a series of gear teeth 17 situated along a surface of the slot 15. Second member 20 includes a portion 22 longitudinally movably received within the interior 16 of the first member 14. As illustrated in FIG. 1, a crown gear-like ring 52 has been provided on the underside of each of base members 14, 20. The rings 52 may be attached to the base members 14 and 20 by any suitable means or may be formed with the base members 14 and 20 themselves. The purpose of rings 52 will be explained subsequently.

The base 12 further includes means 26 rotatably coupled to portion 22 of base member 20 for incrementally adjusting the distance between the distal portions 18 and 24 of the base members 14 and 20 respectively. Incremental adjusting means 26 includes a spur gear 28 fixed to a rotatable shaft 30. A knob 32 is attached to shaft 30 for rotation by the speculum operator to rotate gear 28. The spur gear 28 includes a plurality of teeth which engage teeth 17 situated along the surface of slot 15 in base member 14. When the speculum operator rotates the knob 32, the distal portions 18 and 24 of the base members 14 and 20, respectively, are adjusted to a desired separation. The spur gear 28 can be formed separately from, or formed on, the knob 32.

Referring to FIGS. 4 and 5, the incremental adjusting means 26 further includes means 40 for maintaining a desired separation between the distal ends 18 and 24 of the base members 14 and 20. Referring specifically to FIG. 5, means 40 includes a rib 44 situated on the back side of spur gear 28 which engages one of two slots 42 formed in portion 22 of base member 20. By engaging rib 44 in one of slots 42, spur gear 28 is prevented from further rotation until the speculum operator desires to change the distance between the distal portions 18 and 24 of base members 14 and 20.

As illustrated in FIG. 4, a head 34 is provided on the end of shaft 30 opposite knob 32. Head 34 is located in a recess 39 in member 20. Head 34 retains a spring washer 36. The speculum operator disengages rib 44 from a slot 42 by pulling hand grip 32 outward and engages rib 44 in a slot 42 by releasing the hand grip 32. The speculum operator is thus capable of incrementally adjusting the distance between the distal portions 18 and 24 of base members 14 and 20, respectively, and upon adjustment to a desired distance the speculum operator releases the hand grip 32 to sustain the desired distance until further adjustment is desired. Of course, more than one rib 44 and more than two slots 42 could be provided.

Referring again to FIGS. 1 and 2, speculum 10 further includes two elongated shafts 56 which are rotatably mounted in base members 14 and 20 at their distal portions 18 and 24 respectively. As illustrated in FIG. 2, the shafts 56 extend through apertures 21 located in the distal portions 18 and 24 and into the members 50. The members 40 have crown gear teeth 53 provided in their surfaces adjacent the rings 52. Engagement of teeth 53 with respective rings 52 prevents the shafts 56 from rotating in member 14, 20 from selected rotational positions.

If continuous, rather than discrete adjustment of shafts 56 in members 14, 20 is required, alternative means 54 may be provided instead of rings 52 and cooperating teeth 53 to prevent shaft 56 rotation with respect to members 14, 20. The alternative means 54 is provided for each base member 14 and 20 for sustaining a rotational position of shafts 56 once the speculum operator has independently rotated the shafts to desired rotational positions. The alternative means 54 in FIGS. 1 and 2 are thumbscrews threaded into apertures located in the base members 20 and 14. By advancing screws 54, the shafts 56 are engaged, thereby preventing rotational motion until desired by the speculum operator. Means 54 are shown for purposes of illustration only in the embodiment of FIGS. 1, 2. Means 54 are not necessary to the proper operation of that embodiment. It will be understood that other known means could be utilized for sustaining rotational positions of shafts 56.

Two members 62 are provided for dilating or enlarging an incision, orifice, or meatus. Each member 62 has a distal end 64 for contacting and restraining a portion of the orifice and a proximal end 66 detachably engaging a portion of the elongated rotatable shaft 56. Each member 62 also includes a shoulder 63 adjacent its proximal end 66. Shoulders 63 rest against external body surfaces to support the speculum 10 away from the external body surfaces and prevent, to the greatest possible extent, contamination of the speculum members 14, 20, 56 by organisms on such external surfaces. The edges 69 of the members 62 are beaded, or rounded, to remove any sharp edges from them and minimize the likelihood of tissue damage from edges 69. The elongated rotatable shafts 56 are engaged in sockets 67 provided on the proximal ends 66 of members 62 to mount the members 62 on the distal portions 18 and 24 of base members 14 and 20, respectively.

Each member 62 is elongated, has a concave inner surface 70, and has disposed on the concave inner surface 70 two elongated ribs 72, each of which includes an aperture 74 extending the length of the rib 72. Light from an external light source (not shown) may be directed along the ribs 72 and down the concave inner surfaces 70 of members 62 directly into the orifice or incision. Since members 62 are detachable from the shafts 56, various other shapes and sizes of members 62, such as is illustrated in FIG. 6, may be used with the speculum 10 depending upon the size, shape, or depth of the orifice, incision or meatus desired to be dilated. Furthermore, members 62 may have at least their distal ends 64 covered with a layer of some material (not shown) which is capable of absorbing body fluids such as blood, and may be removed and either sterilized or disposed of after each use without disposing of the entire speculum 10. Accordingly, members 62 may be fabricated from any desirable material such as metal, plastic, etc. Preferably, members 62 will be constructed from a transparent plastic to permit light transmission through them and to permit an examiner to view the walls of the orifice or incision through them.

As further illustrated in FIGS. 1 and 2, the portions of rotatable shafts 56 which are engaged by the detachable members 62 include means 60 on the shafts 56 for preventing members 62 from rotating about shafts 56. Means 60 includes a rectangular portion 61 of each shaft 56. Rectangular portions 61 extend through the sockets 67 in the proximal ends 66 of members 62. Spring washers 58 are interposed between the rectangular portions 61 of shafts 56 and the respective base members 14 and 20 to urge rectangular portions 61 away from members 14, 20 and teeth 53 into engagement with rings 52.

Means 68 are coupled to the proximal ends 66 of members 62 for sustaining desired positions of the members 62 along the shafts 56. The sustaining means 68 include thumbscrews in the apertures located in the proximal ends 66 of members 62. By advancing thumbscrews 68, the extended rectangular portion of shaft 56 is engaged, fixing the positions of the members 62 along the shafts 56. It should be noted that members 62 may be independently rotatably adjusted through various angles and sustained at various positions along their respective shafts 56 independently of each other, permitting the speculum operator the flexibility to adjust the speculum 10 to accommodate various types and shapes of orifices.

Having thus described in detail an embodiment of the invention, the operation of speculum 10 will now be described by referring to FIGS. 1, 3 and 4. The speculum operator can make several adjustments to the speculum 10 in order to adapt the speculum 10 to various sizes, shapes and depths of orifices to be enlarged and/or examined. Means are provided for sustaining the various adjusted positions of the speculum 10 during the examination process, leaving the speculum operator's hands free to perform necessary functions. The speculum operator selects from various shapes and sizes of members 62 the type which is suitable for the orifice to be dilated. The two members 62 may be selected independently and therefore do not necessarily have to be of the same size and shape themselves. Furthermore, as has previously been described, the members 62 may be independently positioned on the shafts 56. Once the speculum operator has selected and attached the desired members 62, the distance between the proximal ends 66 of the members 62 may be incrementally adjusted to permit unobstructed access to the orifice after it is enlarged. This incremental adjustment is accomplished by pulling knob 32 outward and rotating it. As soon as a desired relationship is attained, the speculum operator releases the knob 32, spring washer 36 causing rib 44 to engage one of grooves 42 (FIG. 5) to lock members 14, 20 in a desired relative orientation.

As illustrated by FIG. 3, the distal ends 64 of members 62 may be positioned independently of the positioning of the proximal ends 66 of members 62 by rotating shafts 56. This is achieved by pulling downwardly on knobs 50 against the urging of spring washers 58 (FIGS. 1, 2 and 4) to disengage teeth 53 from rings 52. The knobs 50 are rotated until the shafts 56 reach the desired positions. The knobs 50 are released to permit spring washers 58 to reengage teeth 53 with rings 52. Upon initial entry and contact with the walls of the orifice to be dilated (not shown), the members 62 may be rotated to a position 72 (FIG. 3) wherein the distal ends 64 are in contact with each other, facilitating the initial entry. After entry, the members 62 may be independently rotated by rotating knobs 50, to positions 74 and 76 in which the orifice is enlarged or dilated to a desired width. It is important to note that the initial dilation of the orifice may be accomplished independent of any adjustment of the proximal ends 66 of members 62. In the embodiment utilizing thumbscrews 54 instead of rings 52 and teeth 53, once the desired rotational positions of members 62 have been established, the position of each member 62 may be independently locked by a thumbscrew 54. After the initial dilation of the orifice has been achieved, the distance between the proximal ends 66 of members 62 may be further incrementally increased in order to widen further the dilation or may be incrementally decreased in order to lessen the dilation.

Figure 8:
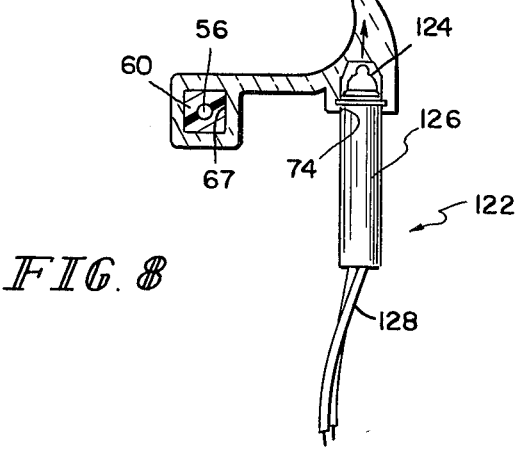
FIG. 8 is a fragmentary sectional view of the apparatus of FIG. 7, taken generally along section lines 8—8 thereof.

Referring to the embodiment of the invention illustrated in FIGS. 7–8, those components performing the same or similar functions as the corresponding elements in the embodiment of FIGS. 1≠6 are numbered similarly.

In FIG. 7, the speculum 10 includes base 12 having first and second members 14 and 20, respectively, adjustably coupled to each other. First member 14 includes hollow interior 16. Second member 20 includes a portion 22 longitudinally movably received within the interior 16 of the first member 14. As illustrated in FIG. 7, a pin 53 is formed on each member 50. A plurality of pockets 52 are provided in each member 14, 20 to receive the pins 53 in each of various selected orientations of the contacting members 62 in this embodiment. The pins 53 are urged upward into engagement with pockets 52 in this embodiment by coil springs 58.

The base 12 further includes means 26 rotatably engaging portion 22 of base member 20 for incrementally adjusting the distance between the distal portions 18 and 24 of the base members 14 and 20, respectively. Incremental adjusting means 26 in this embodiment includes a threaded shaft 28 rotatably engaged in the end 18 of base member 14. Threaded shaft 28 includes a knob 32 rotatable by the speculum operator to rotate shaft 28. The shaft threads engage a bearing 17 which is situated in a bore 115 in the base member 14 and spring loaded into engagement with the troughs in the threads of shaft 28 by a coil spring 116 which is captured between the bearing 17 and a threaded plug 117. When the speculum operator rotates the knob 32, the distal portions 18 and 24 of the base members 14 and 20, respectively, are adjusted to a desired separation. The pitch of the threads on shaft 28 is such that this adjustment will be maintained even under substantial load.

For the purpose of providing light, especially during certain types of surgical procedures, a light source may be coupled to the members 62 through a fiber optic material, such as flexible glass fiber or one of certain types of acrylic resins, such as polymethylmethacrylate. The light source and optical waveguide are constructed as an attachment to a speculum of the type described herein, which may be used as a plastic vaginal speculum or proctoscope, or an abdominal retractor.

In the embodiment of FIGS. 7–8, each contacting member 62 is provided with a socket 74 adjacent its respective shaft 56. Sockets 74 are adapted to receive light sources 122. The light source 122 shown in FIG. 8 includes lamp bulb 124 which extends into the socket 74, a bulb receptacle 126 and wires 128 connecting receptacle 126 to a power source (not shown). The light source could be battery operated. Light from the lamp bulb 124 is guided to the distal end 64 of its respective member 62 by the material from which member 62 itself is constructed. Several suitable materials having optical wave guiding properties are known. Among them is polymethylmethacrylate (LUCITE or PLEXIGLAS). Light from source 122 is directed by the configuration of the material in member 62 down the concave inner surfaces 70 of members 62 directly into the orifice or incision. As with the embodiment of FIGS. 1–6, the operator of the speculum of FIGS. 7 and 8 can make several adjustments to the speculum 10 in order to adapt the speculum 10 to various sizes, shapes, and depths of orifices to be enlarged and/or examined. The speculum operator selects from various shapes and sizes of members 62 the type which is suitable for the orifice to be dilated. The distance between the proximal ends 66 of the members 62 may be adjusted to permit unobstructed access to the orifice after it is enlarged. This adjustment is accomplished by rotating knob 32.

The distal ends 64 of members 62 may be positioned independently of the positioning of the proximal ends 66 of members 62 by pulling knobs 50 downward against the urging of coil springs 58 to move pins 53 from pockets 52 and rotating knobs 50. Once desired rotational positions of members 62 have been established, the position of each member 62 may be independently locked by releasing knobs 50 to reengage pins 53 and pockets 52.

The embodiments and methods of operation described hereinabove are not to be construed as excluding other embodiments or modes of operation of the speculum 10.

The construction illustrated, with the base members 14, 20 out of the way, permits easy access to the orifice with surgical instruments and the like.

Figure 9:
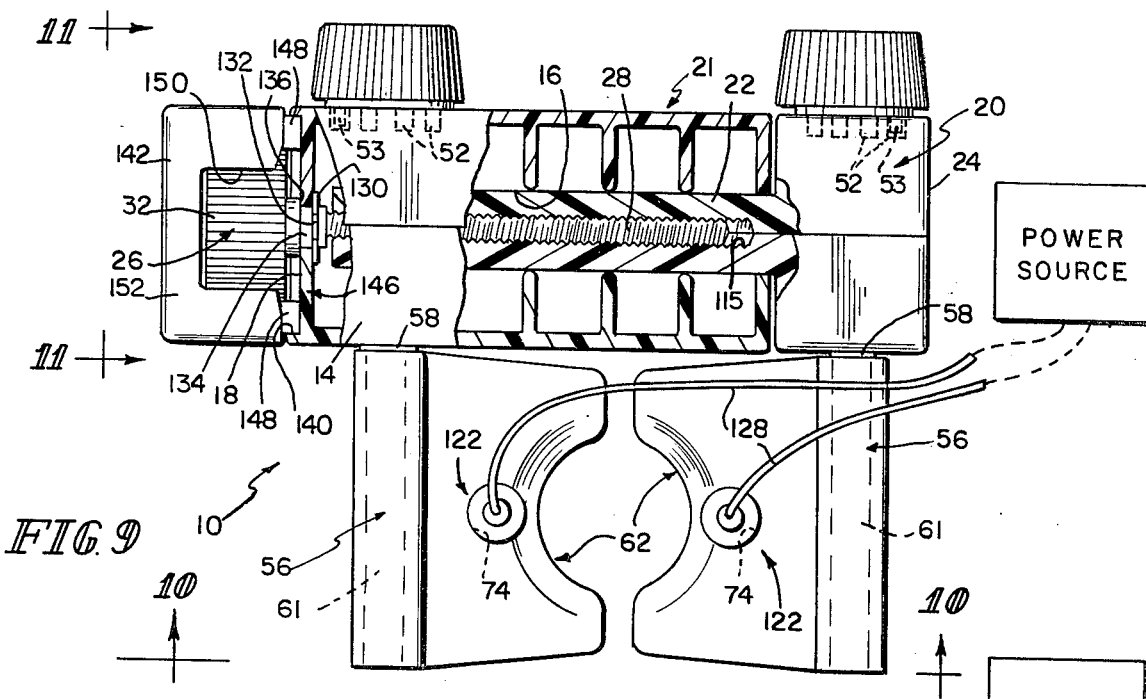
FIG. 9 is a partly fragmentary elevational view of another alternative structure to those illustrated in FIGS. 1-5 and 7-8.
Figure 10:
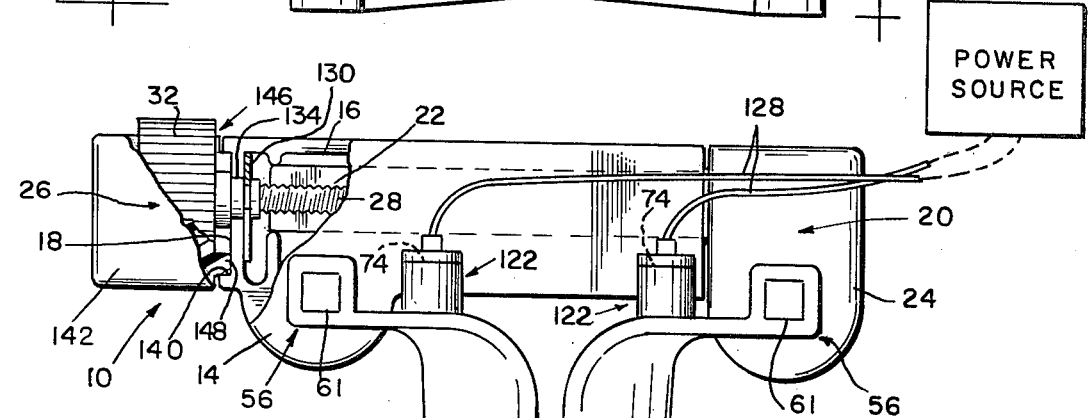
FIG. 10 is a top plan view, partly fragmentary, taken along section lines 10—10 of FIG. 9.
Figure 11:
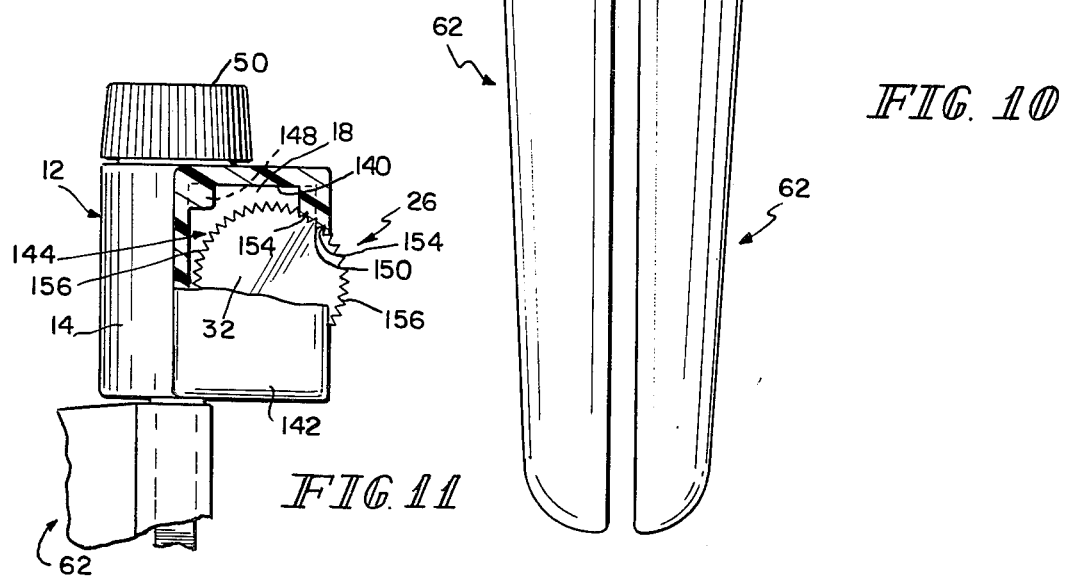
FIG. 11 is a fragmentary end elevational view, taken generally along section lines 11—11 of FIG. 9.

Referring to the embodiment of the invention illustrated in FIGS. 9-11, those components performing the same or similar functions as the corresponding elements in the embodiments of FIGS. 1-6 and 7-8 are numbered similarly.

In FIGS. 9-11, the speculum 10 includes a base 12 having first and second members 14, 20 respectively, adjustably coupled to each other. Each of the members 14, 20 in this embodiment is molded, e.g., from a synthetic plastic material, in two halves which are subsequently joined together. First member 14 includes the hollow interior 16. Second member 20 includes a portion 22 longitudinally movable within the interior 16.

In this embodiment, as in the embodiment illustrated in FIGS. 7-8, a locating pin 53 is formed in each member 50, and a plurality of cooperating pockets 52 are provided on each of members 14, 20 to receive the locating pins in each of various selected orientations of the contacting members 62. The pins are urged upwardly into engagement with the pockets of this embodiment by spring washers 58 interposed between the rectangular portions 61 of shafts 56 and the respective base members 14, 20.

The base member 12 of this embodiment includes, as incremental adjustment means 26, a threaded shaft 28 rotatably captured in the end 18 of base member 14 by a C-ring 130 provided in an annular groove 132 on a projecting bearing portion 134 of an adjustment knob 32. Knob 32 is provided with a stop surface 136. The end 18 of base member 14 is rotatably captured between the C-ring 130 and the surface 136.

End 18 of base member 14 is formed to provide a generally rectangular recess 140. An end cap 142 has an open center 144 (FIG. 11) and an open end 146 (FIGS. 9-10) sized slidably to engage knob 32. Tabs 148 are provided at the open end 146 to engage in the recess and hold the cap on end 18. The cap includes a longitudinally extending slot 150 (FIGS. 9, 11) in its sidewall 152. The edges of the slot 150 are grooved, as indicated at 154 (FIG. 11) to engage the splines 156 of knob 32. In this embodiment, the knob 32 is held in position by the engagement of the grooves 154 with the splines 156 when cap 142 is placed over the knob 32 and the tabs 148 are engaged in recess 140.

The shaft 28 threads engage in a threaded bore 115 provided in the base member 22. When the speculum operator rotates the knob 32, the distal portions 18 and 24 of base members 14, 20, respectively, are adjusted to a desired separation.

For the purpose of providing light, each contacting member 62 is provided with a socket 74 adjacent its respective shaft 56. The sockets 74 support lamps 122. Conductors 128 connect the sources 122 to a power source (illustrated diagrammatically).

Figure 12:
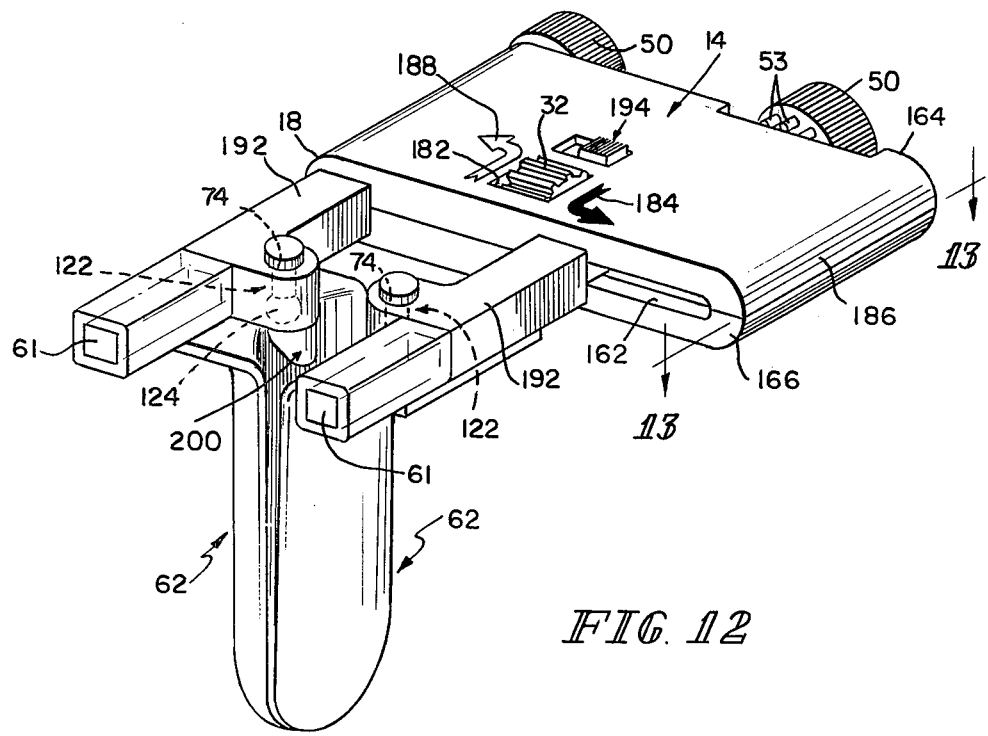
FIG. 12 is a perspective view of another alternative structure.
Figure 13:
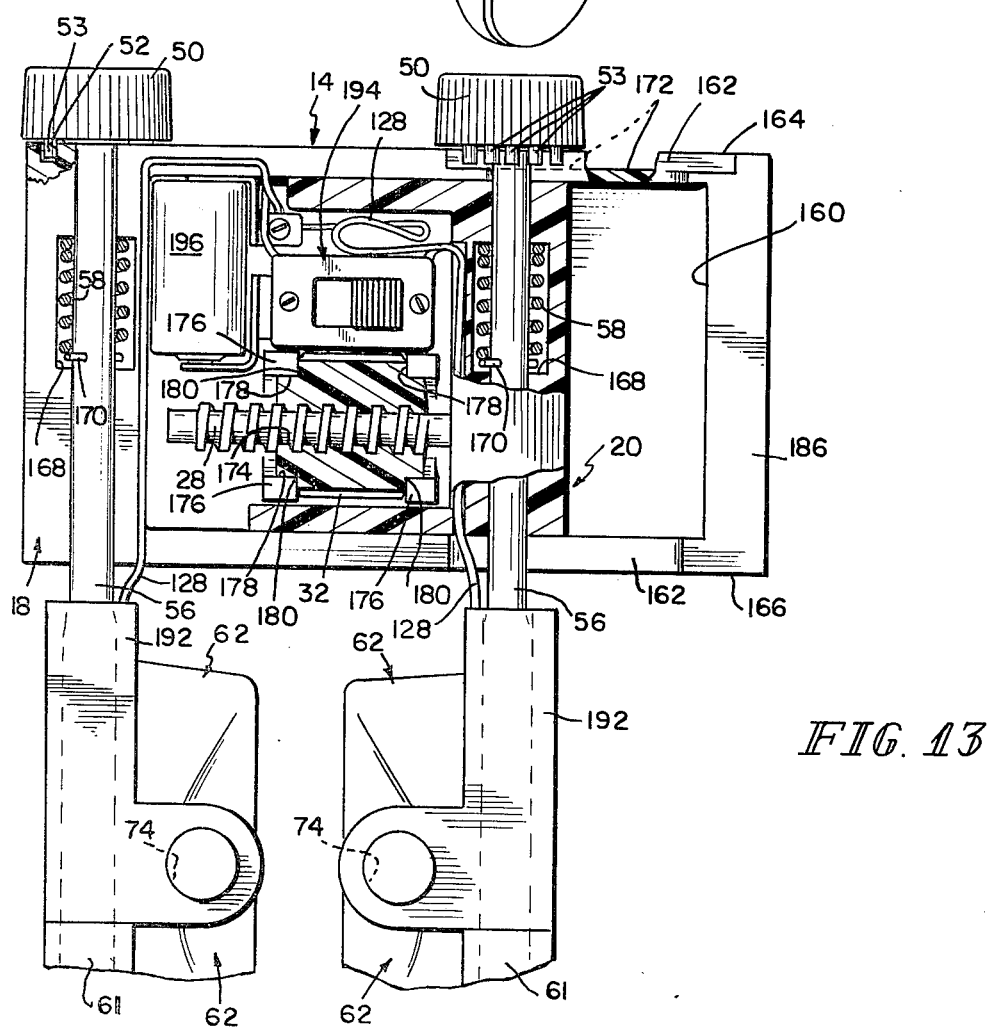
FIG. 13 is a sectional view of the apparatus of FIG. 12, taken generally along section lines 13—13 thereof.

Referring now to the embodiment of the invention illustrated in FIGS. 12-13, those elements performing the same or similar functions as the corresponding elements in the embodiments of FIGS. 1-5, 7-8 and 9-11 are numbered similarly.

In this embodiment, first member 14 is constructed from, for example, moldable plastic material. First member 14 is constructed in the form of a case having a hollow interior 160. Slots 162 are provided in two opposite walls 164, 166 of the case 14. Member 20 (FIG. 13) is constructed in the form of a slide movably mounted in the interior 160. A pin 53 is formed on each of the knob members 50. A plurality of pockets 52 are provided in member 14 adjacent the knob 50 at end 18 to receive pin 53 of that knob 50 in each of various selected orientations of the contacting members 62. The pin 53 is urged into engagement with the pocket 52 by a coil spring 58 which is provided in a cavity 168 in first member 14 adjacent end 18. The coil spring 58 works against a pin 170 protruding from the shaft 56 rotatably mounted in end 18.

A similar arrangement for the knob member 50 and shaft 56 is provided on member 20, with a cavity 168 for the spring 58. The spring 58 works against a pin 170 which protrudes from shaft 56. To prevent rotation of the shaft 56 associated with second member 20, a plurality of pins 53 are provided on knob member 50 which are adapted for insertion into the slot 162 in wall 164. One of pins 53 selectively engages the slot 162 to prevent rotation of the member 50, and thereby the shaft 56 and contacting member 62 associated with member 20. To prevent interference between the other pins 53 associated with second member 20, the member 14 wall 164 has a reduced thickness, as illustrated at 172 in FIG. 13, around the slot 162 in wall 164. This configuration permits free sliding movement of member 20 without interference between the slot 162 or wall 164 and pins 53 on the member 20 knob 50.

Member 20 is further provided with a rigidly attached, longitudinally extending threaded shaft 28. Shaft 28 rotatably mounts a knob 32 with a threaded central bore 174. Knob 32 in this embodiment is rotatably mounted in the case-like first member 14 between two end supports 176, with the end supports providing bearing surfaces 178 and the knob 32 providing cooperating bearing surfaces 180. Knob 32 is accessible through an opening 182 in one of the molded halves of base member 14. Rotation of the knob in a first direction, indicated by arrow 186 (FIG. 12) on member 14, results in movement of second member 20, and its contacting member 62 toward the end 186 of first member 14. Rotation of knob 32 in a second direction, indicated by arrow 188 on member 14, causes member 20 to move toward end 18 of member 14.

The shafts 56 are provided with permanently mounted portions 192 including sockets 74 adapted to receive the light sources 122, and conductors 128 which are threaded or molded into the shaft portions 192. The conductors 128 extend into the interior 160 of member 14 where they are connected through a switch 194 to a dry cell 196. The contacting members 62 in this arrangement are adapted to fit slidably and snugly over the square or rectangular ends 61 of shafts 56 above shaft portions 192. Each contacting member 62 is provided with a lens portion 200 (FIG. 12) which is in intimate contact with the lamp bulb 124 provided in a respective socket 74 when the contacting members 62 are in position on the shaft 56 ends, as illustrated in FIG. 12. In this arrangement, the lamps 122 are permanently mounted on the speculum 10, and need not be removed from, or replaced in, lamp sockets 74 each time the contacting members 62 are changed.

Figure 14:
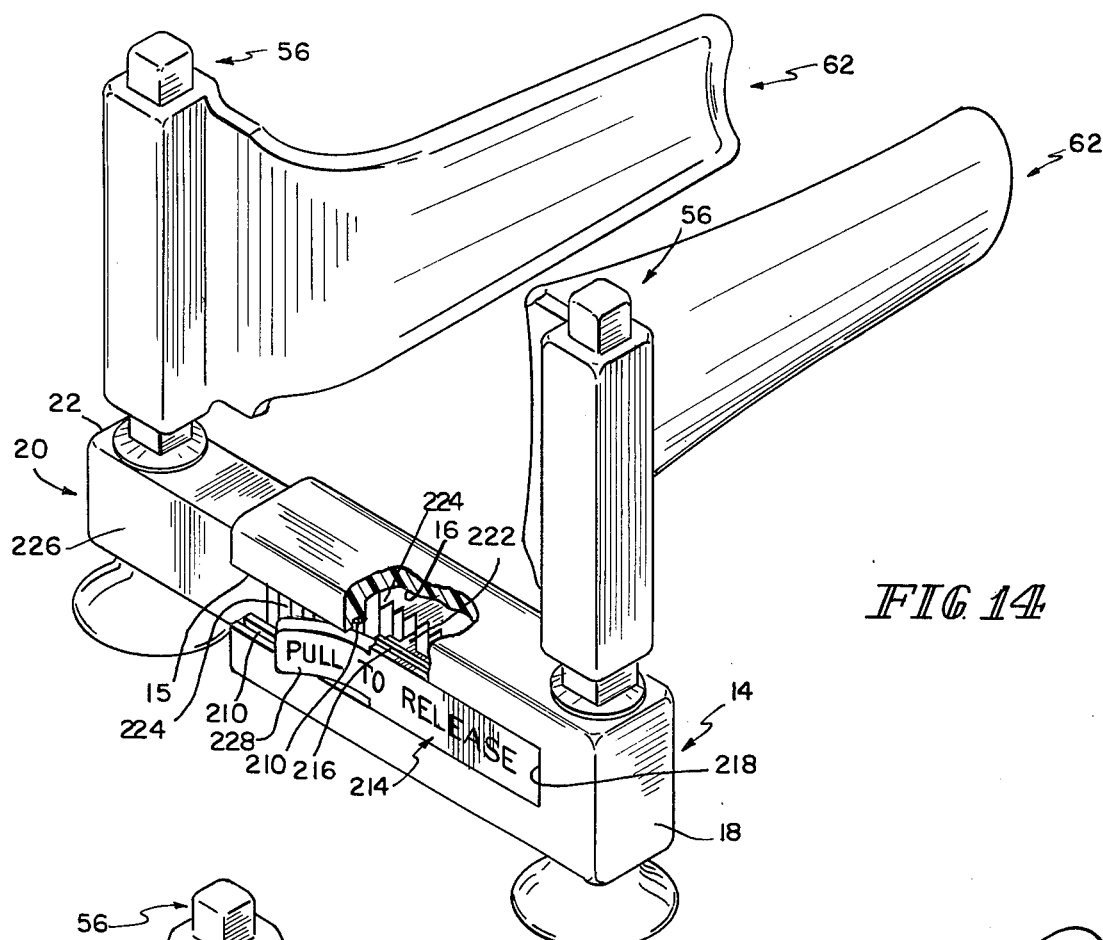
FIG. 14 is a partly fragmentary perspective view of another alternative structure.
Figure 15:
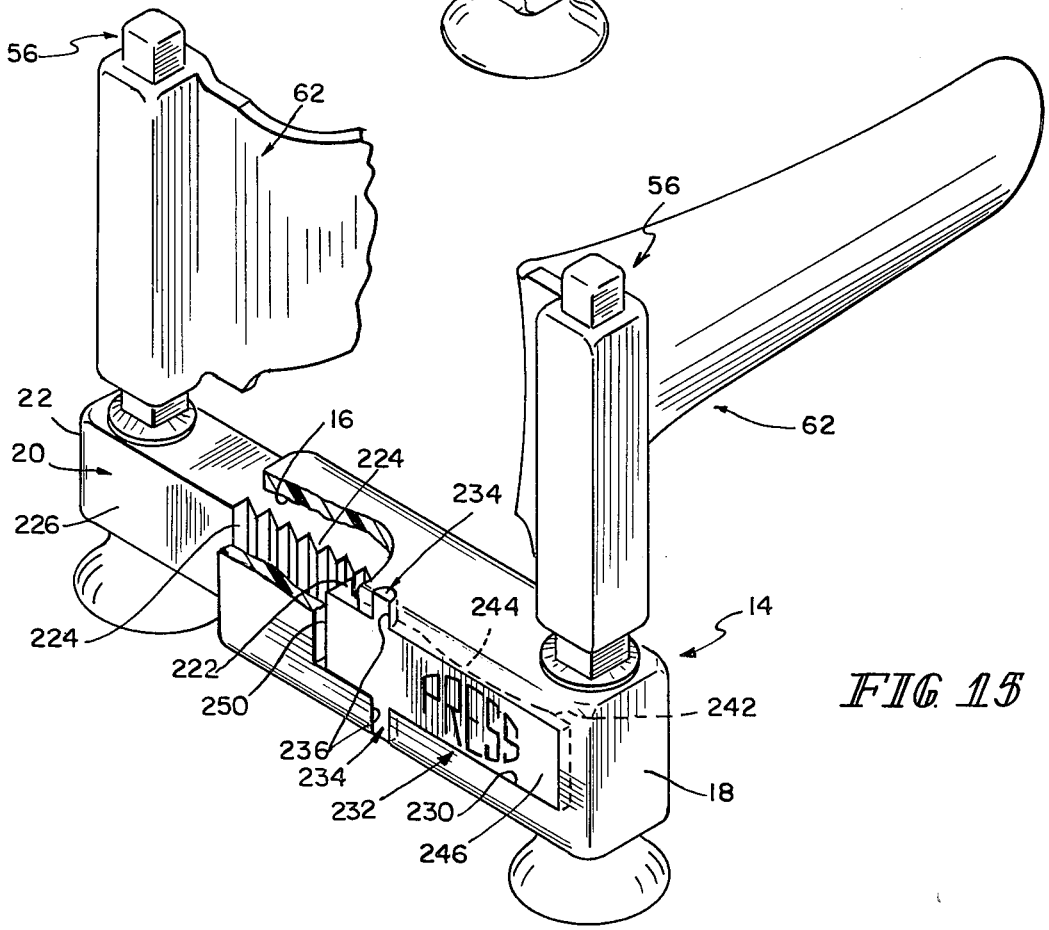
FIG. 15 is a partly fragmentary perspective view of yet another alternative structure.

In the embodiments of the invention illustrated in FIGS. 14-15, those elements performing the same or similar functions as the corresponding elements in the embodiments of FIGS. 1-5, 7-8, 9-11 and 12-13 are numbered similarly.

In the embodiment of FIG. 14, the slot 15 formed in first member 14 has two opposite edges, each provided with a shallow, longitudinally extending groove 210. A tab 214 is constructed from a flexible, semi-rigid synthetic material, such as nylon. Tab 214 has opposite longitudinally extending tongues 216 (only one of which is shown) for engagement with the grooves 210 as the tab 214 is slidably inserted into the slot 15 to rest against the end 218 of the slot 15. The tab 214 is provided with a transversely extending tooth or pawl 222 on its side facing the hollow interior 16.

Base member 20 includes a series of transversely extending ratchet teeth 224 on its side 226 facing the slot 15. The tongues 216 on tab 214 terminate adjacent pawl 212 such that an outward pull on a portion 228 of tab 214 moves pawl 222 clear of engagement with ratchet teeth 224. Adjustment is made of the distance between the shafts 56 mounted on respective members 14, 20 by disengaging pawl 222 from the teeth 224 and manually sliding member 20 to a desired projection from member 14. Pawl 222 is then pushed into engagement with a ratchet tooth 224 to retain members 14, 20 in the selected projected orientations.

In the embodiment of FIG. 15, member 20 is constructed as in the embodiment of FIG. 14 with a series of ratchet teeth 224 on its side 226 facing an opening 230 in member 14. In this embodiment, a tab 232 is mounted in the opening 230 by engagement of a pair of ears 234 in slots 236 which intersect opening 230. Tab 232 is thereby pivotally mounted about ears 234 in the opening 230. The inner side 242 of tab 232 is provided with a transversely extending concave, or hollow, region 244. The tab 232 is constructed from the same type of flexible synthetic material as tab 214 in FIG. 14. It will be appreciated that pressure in the outside surface 246 of the tab 232 opposite the region 244 will result in an outward pivotal motion of the tab 232 end 250 having the pawl 222. Such outward motion will result in disengagement of the pawl 222 from the ratchet teeth 224 provided in member 20 and permit sliding movement of the member 20 in the interior 16 of member 14 for adjustment purposes. Releasing the pressure on the tab 232 opposite concave portion 244 permits the tab 232 to flex back about the pivotal mounting ears 234 such that pawl 222 returns into engagement with the ratchet teeth 224, locking members 14, 20 in a selected orientation.

What is claimed is:

1. A speculum comprising a base including first and second base members for movement with respect to one another, means for adjustng the distance between a distal portion of the first base member and a distal portion of the second base member, means for connecting the adjusting means to one of the first and second base members, first and second shafts, means rotatably supporting each shaft from the distal portion of a respective one of the first and second members, and means for dilating an orifice, the dilating means being provided on the first and second shafts, the dilating means being responsive to adjustment of the first and second members and rotation of the first and second shafts, said means for adjusting the distance between the distal portions of the first and second members including a threaded shaft mounted in one of the first and second base members, means engaging the threaded shaft on the other of the first and second base members, and means for selectively rotating one of either the threaded shaft or means engaging the threaded shaft to advance and retract said other base member with respect to said one base member.

2. The apparatus of claim 1 wherein the threaded shaft is rotatably mounted with respect to one of the base members and the means engaging the threaded shaft is stationarily mounted with respect to the other of the base members.

3. The apparatus of claim 1 wherein the threaded shaft is stationarily mounted with respect to one of the base members and the means engaging the threaded shaft is rotatably mounted with respect to the other of the base members.

4. A speculum comprising a base including a first base member providing an interior and a second base member for movement within said interior, means for adjusting the distance between a distal portion of said first base member and a distal portion of said second base member, means for connecting said adjusting means to one of said base members, two shafts, means rotatably coupling each of the shafts to the distal portion of a respective base member, and means for dilating an orifice, the dilating means being provided on said shafts, said dilating means responsive to selective adjustment of said first and second base members and rotation of said elongated shafts selectively to dilate the orifice, said means for adjusting said distance between said distal portions of said first and second base members including a threaded shaft mounted on one of said base members and means for engaging said threaded shaft on the other of said base members, and means for selectively rotating one of either said threaded shaft or said means engaging said threaded shaft selectively to vary said distance.

5. The apparatus of claim 4 wherein said threaded shaft is rotatably mounted on said one of said base members and said means engaging said threaded shaft comprises a threaded passageway provided in said other of said base members.

6. The apparatus of claim 5 in which said one of said base members includes journal mounting means for rotatably mounting said threaded shaft.

7. The apparatus of claim 4 wherein said threaded shaft is stationarily mounted on said one of said base members and said means engaging said threaded shaft comprises means rotatably mounted on said other of said base members and including a threaded passageway engaging said threaded shaft.

8. The apparatus of claim 7 wherein said means for selectively rotating one of said shaft and means engaging said shaft includes a hand-manipulable wheel.

9. The apparatus of claim 8 wherein said threaded passageway is provided through the axis of said wheel.

10. A speculum comprising a base including first and second base members for movement with respect to one another, means for adjusting the distance between a distal portion of the first base member and a distal portion of the second base member, means for connecting the adjusting means to one of the first and second base members, first and second shafts, means rotatably supporting said first shaft from a distal portion of the first base member, means supporting said second shaft from a distal portion of the second base member, blade-like contacting members for dilating an orifice, the contacting members being provided on the first and second shafts, the contacting members being responsive to adjustment of the first and second base members and rotation of the first shaft, and means engageable with said first shaft for independently sustaining a desired rotational position of one of the contacting members associated with the first shaft, such position-sustaining means including a fixed projection on one of said first base member and first shaft and a plurality of sockets on the other of said first base member and first shaft, each socket sized to receive the projection, and spring means urging said projection and sockets together so as to urge the projection into engagement with a selected one of said sockets to prevent rotation of said first shaft with respect to said first base member.

11. The apparatus of claim 10 wherein the means for supporting said second shaft from a distal portion of the second base member includes means for rotatably supporting the second shaft from a distal portion of the second base member, and means engageable with the second shaft for independently sustaining a desired rotational position of the contacting member associated with the second shaft.

12. The apparatus of claim 11 wherein the means for independently sustaining the desired rotational position of the second shaft includes a fixed projection on one of the second shaft and second base member and a plurality of sockets on the other of the second shaft and second base member, each socket sized to receive the projection, and spring means urging said projection and sockets together so as to urge the projection into engagement with a selected one of said sockets to prevent rotation of the second shaft with respect to the second base member.

13. A speculum including at least two blade-like contacting members for dilating an orifice, a shaft for supporting each contacting member, means for connecting each contacting member to a respective shaft, each contacting member having a proximal end engaging a respective shaft and a distal end for insertion into the orifice, a base including means for rotatably supporting a first one of said shafts and for supporting the other of said shafts, and means for adjusting the distance between the distal ends of the contacting members including first means on the base and second means on said first one of the shafts engaging the first means in at least selected positions of said first one of the shafts to prevent rotation of said first one of the shafts with respect to said base, the base including a passageway for said first one of the shafts, said first one of the shafts being rotatably received in its passageway, the means on the base including a plurality of sockets on the base surrounding said passageway, and said second means including a fixed projection on said first one of the shafts, and means for yieldably urging said projection into engagement with a selected one of said sockets selectively to position said first one of the shafts with respect to said base.

14. A speculum comprising a base including first and second base members for movement with respect to one another, means for adjusting the distance between a distal portion of the first base member and a distal portion of the second base member, means for connecting the adjusting means to one of the first and second base members, first and second shafts, means rotatably supporting said first shaft from a distal portion of the first base member, means supporting said second shaft from a distal portion of the second base member, blade-like contacting members for dilating an orifice, the contacting members being provided on the first and second shafts and extending generally perpendicular to the first and second shafts, the contacting members being responsive to adjustment of the first and second base members and rotation of the first shaft, and means engageable with said first shaft for independently sustaining a desired rotational position of the contacting member associated with the first shaft, such position-sustaining means including a fixed projection on one of said first base member and first shaft and a plurality of sockets on the other of said first base member and first shaft, each socket sized to receive the projection, and spring means urging the projection into engagement with a selected one of said sockets to prevent rotation of said first shaft with respect to said first base member.

15. The apparatus of claim 14 wherein the means for supporting the first and second shafts includes means for supporting the shafts such that their axes are generally parallel and adjustment of the distance between the distal portions of the first and second base members adjusts the distance between the first and second shaft axes.

16. The apparatus of claim 14 wherein the means for supporting said second shaft from a distal portion of the second base member includes means for rotatably supporting the second shaft from a distal portion of the second base member, and means engageable with the second shaft for independently sustaining a desired rotational position of the contacting member associated with the second shaft.

17. The apparatus of claim 16 wherein the means for independently sustaining the desired rotational position of the second shaft includes a fixed projection on one of the second shaft and second base member and a plurality of sockets on the other of the second shaft and second base member, each socket sized to receive the projection, and spring means urging the projection into engagement with a selected one of said sockets to prevent rotation of the second shaft with respect to the second base member.

18. A speculum including at least two blade-like contacting members for dilating an orifice, a shaft for supporting each contacting member, means for connecting each contacting member to a respective shaft, each contacting member having a proximal end engaging a respective shaft for supporting each contacting member generally perpendicular to a respective shaft and a distal end for insertion into the orifice, a base including means for rotatably supporting a first one of said shafts and for supporting the other of said shafts, and means for adjusting the distance between the distal ends of the contacting members including first means on the base and second means on said first one of the shafts engaging the first means in at least selected positions of said first one of the shafts to prevent rotation of said first one of the shafts with respect to said base, the base including a passageway for said first one of the shafts, said first one of the shafts being rotatably received in its passageway, the first means on the base including a plurality of sockets on the base surrounding said passageway, and said second means including a fixed projection on said first one of the shafts, and means for yieldably urging said projection into engagement with a selected one of said sockets selectively to position said first one of the shafts with respect to said base.

* * * * *

UNITED STATES PATENT AND TRADEMARK OFFICE
CERTIFICATE OF CORRECTION

PATENT NO. : 4,263,899
DATED : April 28, 1981
INVENTOR(S) : Kermit H. Burgin

It is certified that error appears in the above-identified patent and that said Letters Patent are hereby corrected as shown below:

In the inventor's address, change "Whitestone" to -- Whitestown --.

Column 1, line 25, insert a colon after "illustrative".

Column 4, line 56, "the" (first occurrence) should be -- threaded --.

Column 5, line 58, the line should read -- in the embodiment of Figs. 1-6 are numbered simi- --.

Column 6, line 12, after "shaft" (second occurrence), insert -- 28 --.

Column 9, line 40, "in" should be -- on --; line 50, (claim 1, line 3) "adjusting" is misspelled.

Signed and Sealed this

Fifteenth Day of September 1981

[SEAL]

Attest:

GERALD J. MOSSINGHOFF

Attesting Officer    Commissioner of Patents and Trademarks